United States Patent
Sartor et al.

(10) Patent No.: US 10,813,685 B2
(45) Date of Patent: Oct. 27, 2020

(54) SINGLE-HANDED OPERABLE SURGICAL INSTRUMENT INCLUDING LOOP ELECTRODE WITH INTEGRATED PAD ELECTRODE

(71) Applicant: COVIDIEN LP, Mansfield, MA (US)

(72) Inventors: Joe D. Sartor, Longmont, CO (US);
John Westwood, San Jose, CA (US);
Aaron D. Leyva, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 1054 days.

(21) Appl. No.: 14/841,975

(22) Filed: Sep. 1, 2015

(65) Prior Publication Data
US 2016/0089199 A1 Mar. 31, 2016

Related U.S. Application Data

(60) Provisional application No. 62/055,328, filed on Sep. 25, 2014.

(51) Int. Cl.
*A61B 18/14* (2006.01)
*A61B 18/00* (2006.01)
*A61B 18/16* (2006.01)

(52) U.S. Cl.
CPC .......... *A61B 18/1482* (2013.01); *A61B 2018/00601* (2013.01); *A61B 2018/1407* (2013.01); *A61B 2018/1475* (2013.01); *A61B 2018/162* (2013.01)

(58) Field of Classification Search
CPC ...... A61B 18/1482; A61B 2018/00601; A61B 2018/1407; A61B 2018/1475
See application file for complete search history.

(56) References Cited

U.S. PATENT DOCUMENTS

| | | |
|---|---|---|
| 749,689 A | 1/1904 | Houghton |
| 1,952,617 A | 3/1934 | Wappler |
| 1,963,636 A | 6/1934 | Wappler |
| 1,987,015 A | 7/1934 | Wappler |
| 2,002,559 A | 5/1935 | Wappler |
| 2,008,525 A | 7/1935 | Wappler |

(Continued)

FOREIGN PATENT DOCUMENTS

| | | |
|---|---|---|
| DE | 2415263 A1 | 10/1975 |
| DE | 02514501 A1 | 10/1976 |

(Continued)

OTHER PUBLICATIONS

Examination Report issued in corresponding European application No. 14 154 456.9 dated Aug. 11, 2015.

(Continued)

*Primary Examiner* — Michael F Peffley
*Assistant Examiner* — Samantha M Good
(74) *Attorney, Agent, or Firm* — Carter, DeLuca & Farrell LLP

(57) ABSTRACT

A bipolar electrosurgical instrument includes a handle portion, a shaft extending from the handle portion, a pad electrode coupled to the distal end of the shaft, and a loop electrode configured to be selectively transitioned from a deployed configuration, wherein the loop electrode extends outwardly from a distal end of the shaft in a manner capable of receiving tissue, to a non-deployed configuration, wherein the loop electrode is disposed proximate to the distal end of the shaft, to treat tissue.

7 Claims, 10 Drawing Sheets

(56) References Cited

U.S. PATENT DOCUMENTS

| | | |
|---|---|---|
| 2,011,169 A | 8/1935 | Wappler |
| 2,054,149 A | 9/1936 | Wappler |
| 2,442,966 A | 6/1948 | Wallace |
| 2,532,043 A | 11/1950 | Wallace |
| 3,149,633 A | 9/1964 | Zingale |
| 3,752,159 A | 8/1973 | Wappler |
| 3,856,015 A | 12/1974 | Iglesias |
| 4,011,872 A | 3/1977 | Komiya |
| 4,024,869 A | 5/1977 | Bonnet |
| 4,060,087 A | 11/1977 | Hiltebrandt et al. |
| 4,068,667 A | 1/1978 | Iglesias |
| 4,116,198 A | 9/1978 | Roos |
| 4,134,406 A | 1/1979 | Iglesias |
| 4,202,338 A | 5/1980 | Bitrolf |
| 4,294,254 A | 10/1981 | Chamness |
| 4,311,143 A | 1/1982 | Komiya |
| 4,493,320 A | 1/1985 | Treat |
| 4,503,855 A | 3/1985 | Maslanka |
| 4,718,419 A | 1/1988 | Okada |
| 4,733,662 A | 3/1988 | DeSatnick et al. |
| 4,905,691 A | 3/1990 | Rydell |
| 5,026,371 A | 6/1991 | Rydell et al. |
| 5,066,295 A | 11/1991 | Kozak et al. |
| 5,078,716 A | 1/1992 | Doll |
| 5,192,280 A | 3/1993 | Parins |
| 5,197,964 A | 3/1993 | Parins |
| 5,207,686 A | 5/1993 | Dolgin |
| 5,282,799 A | 2/1994 | Rydell |
| 5,290,284 A | 3/1994 | Adair |
| 5,318,564 A | 6/1994 | Eggers |
| 5,417,697 A | 5/1995 | Wilk et al. |
| 5,423,813 A | 6/1995 | Kaiser et al. |
| 5,460,629 A | 10/1995 | Shlain et al. |
| 5,462,553 A | 10/1995 | Dolgin |
| 5,569,244 A | 10/1996 | Hahnen |
| 5,597,107 A | 1/1997 | Knodel et al. |
| 5,658,280 A | 8/1997 | Issa |
| 5,810,764 A | 9/1998 | Eggers et al. |
| 5,817,093 A | 10/1998 | Williamson, IV et al. |
| 5,843,019 A | 12/1998 | Eggers et al. |
| 5,902,300 A | 5/1999 | Hahnen et al. |
| 5,971,994 A | 10/1999 | Fritzsch |
| 6,013,076 A | 1/2000 | Goble et al. |
| 6,015,415 A | 1/2000 | Avellanet |
| 6,050,995 A | 4/2000 | Durgin |
| 6,071,283 A | 6/2000 | Nardella et al. |
| 6,080,152 A * | 6/2000 | Nardella ............ A61B 18/1485 606/46 |
| 6,093,186 A | 7/2000 | Goble |
| 6,142,992 A | 11/2000 | Cheng et al. |
| 6,152,922 A | 11/2000 | Ouchi |
| 6,235,020 B1 | 5/2001 | Cheng et al. |
| 6,235,026 B1 | 5/2001 | Smith |
| 6,296,636 B1 | 10/2001 | Cheng et al. |
| 6,440,138 B1 | 8/2002 | Reiley et al. |
| 6,482,201 B1 | 11/2002 | Olsen et al. |
| 6,517,539 B1 | 2/2003 | Smith et al. |
| 6,632,193 B1 | 10/2003 | Davison et al. |
| 6,730,084 B2 | 5/2004 | Held |
| 6,730,097 B2 | 5/2004 | Dennis |
| 6,743,228 B2 | 6/2004 | Lee et al. |
| 6,773,432 B1 | 8/2004 | Clayman et al. |
| 6,827,717 B2 | 12/2004 | Brommersma et al. |
| 6,837,888 B2 | 1/2005 | Ciarrocca et al. |
| 6,852,108 B2 | 2/2005 | Barry et al. |
| 6,852,111 B1 | 2/2005 | Lieber |
| 6,860,848 B2 | 3/2005 | Wosnitza et al. |
| 6,972,017 B2 | 12/2005 | Smith et al. |
| 6,974,453 B2 | 12/2005 | Woloszko et al. |
| 7,008,420 B2 | 3/2006 | Okada |
| 7,037,307 B2 | 5/2006 | Dennis |
| 7,104,990 B2 | 9/2006 | Jenkins et al. |
| 7,118,569 B2 | 10/2006 | Snay et al. |
| 7,128,742 B2 | 10/2006 | Ohyama et al. |
| 7,150,097 B2 | 12/2006 | Sremcich et al. |
| 7,762,959 B2 | 7/2010 | Bilsbury |
| 7,887,536 B2 | 2/2011 | Johnson et al. |
| 8,016,827 B2 | 9/2011 | Chojin |
| 8,112,871 B2 | 2/2012 | Brandt et al. |
| 8,114,122 B2 | 2/2012 | Nau, Jr. |
| 8,133,254 B2 | 3/2012 | Dumbauld et al. |
| 8,142,473 B2 | 3/2012 | Cunningham |
| 8,162,965 B2 | 4/2012 | Reschke et al. |
| 8,162,973 B2 | 4/2012 | Cunningham |
| 8,197,479 B2 | 6/2012 | Olson et al. |
| 8,226,650 B2 | 7/2012 | Kerr |
| 8,251,994 B2 | 8/2012 | McKenna et al. |
| 8,257,387 B2 | 9/2012 | Cunningham |
| 8,266,783 B2 | 9/2012 | Brandt et al. |
| 8,277,446 B2 | 10/2012 | Heard |
| 8,282,634 B2 | 10/2012 | Cunningham et al. |
| 8,287,536 B2 | 10/2012 | Mueller et al. |
| 8,292,886 B2 | 10/2012 | Kerr et al. |
| 8,298,243 B2 | 10/2012 | Carlton et al. |
| 8,303,582 B2 | 11/2012 | Cunningham |
| 8,317,787 B2 | 11/2012 | Hanna |
| 8,323,310 B2 | 12/2012 | Kingsley |
| 8,328,803 B2 | 12/2012 | Regadas |
| 8,343,150 B2 | 1/2013 | Artale |
| 8,343,151 B2 | 1/2013 | Siebrecht et al. |
| 8,357,159 B2 | 1/2013 | Romero |
| 8,388,647 B2 | 3/2013 | Nau, Jr. et al. |
| 8,430,876 B2 | 4/2013 | Kappus et al. |
| 8,439,911 B2 | 5/2013 | Mueller |
| 8,469,956 B2 | 6/2013 | McKenna et al. |
| 8,469,957 B2 | 6/2013 | Roy |
| 8,486,107 B2 | 7/2013 | Hinton |
| 8,512,371 B2 | 8/2013 | Kerr et al. |
| 8,535,312 B2 | 9/2013 | Horner |
| 8,568,412 B2 | 10/2013 | Brandt et al. |
| 8,623,017 B2 | 1/2014 | Moses et al. |
| 8,632,539 B2 | 1/2014 | Twomey et al. |
| 8,632,564 B2 | 1/2014 | Cunningham |
| 8,636,761 B2 | 1/2014 | Cunningham et al. |
| 8,679,115 B2 | 3/2014 | Reschke |
| 8,747,413 B2 | 6/2014 | Dycus |
| 8,784,417 B2 | 7/2014 | Hanna |
| 8,795,274 B2 | 8/2014 | Hanna |
| 8,968,314 B2 | 3/2015 | Allen, IV |
| 8,968,358 B2 | 3/2015 | Reschke |
| 9,192,430 B2 | 11/2015 | Rachlin et al. |
| 2001/0009985 A1 | 7/2001 | Durgin et al. |
| 2001/0020167 A1 | 9/2001 | Woloszko et al. |
| 2001/0025177 A1 | 9/2001 | Woloszko et al. |
| 2002/0013583 A1 | 1/2002 | Camran et al. |
| 2002/0072739 A1 | 6/2002 | Lee et al. |
| 2002/0151889 A1 | 10/2002 | Swanson et al. |
| 2002/0165540 A1 | 11/2002 | Bales et al. |
| 2003/0009166 A1 | 1/2003 | Moutafis et al. |
| 2003/0040744 A1 | 2/2003 | Latterell et al. |
| 2003/0109870 A1 | 6/2003 | Lee et al. |
| 2003/0114850 A1 | 6/2003 | McClurken et al. |
| 2003/0125731 A1 | 7/2003 | Smith et al. |
| 2003/0130653 A1 | 7/2003 | Sato et al. |
| 2003/0144661 A1 | 7/2003 | Brommersma et al. |
| 2003/0153909 A1 | 8/2003 | Levinson |
| 2003/0176859 A1 | 9/2003 | Levinson |
| 2003/0181906 A1 | 9/2003 | Boebel et al. |
| 2003/0204188 A1 | 10/2003 | Morrison et al. |
| 2003/0212389 A1 | 11/2003 | Durgin et al. |
| 2003/0216731 A1 | 11/2003 | Dennis |
| 2004/0064139 A1 | 4/2004 | Yossepowitch |
| 2004/0106920 A1 | 6/2004 | Jenkins et al. |
| 2004/0153059 A1 | 8/2004 | Okada |
| 2004/0199159 A1 | 10/2004 | Lee et al. |
| 2004/0220564 A1 | 11/2004 | Ho et al. |
| 2005/0070889 A1 | 3/2005 | Nobis et al. |
| 2005/0085808 A1 | 4/2005 | Nakao |
| 2005/0096650 A1 | 5/2005 | Ouchi |
| 2005/0119652 A1 | 6/2005 | Vetter et al. |
| 2005/0131402 A1 | 6/2005 | Ciarrocca et al. |
| 2005/0131403 A1 | 6/2005 | Chang |
| 2005/0137591 A1 | 6/2005 | Barry et al. |
| 2005/0171531 A1 | 8/2005 | Eliachar et al. |

(56) References Cited

U.S. PATENT DOCUMENTS

| | | |
|---|---|---|
| 2005/0171532 A1 | 8/2005 | Ciarrocca |
| 2005/0209590 A1 | 9/2005 | Terakura |
| 2005/0222568 A1 | 10/2005 | O'Sullivan et al. |
| 2005/0251134 A1 | 11/2005 | Woloszko et al. |
| 2005/0283150 A1 | 12/2005 | Moutafis et al. |
| 2006/0009759 A1 | 1/2006 | Chrisitian et al. |
| 2006/0030846 A1 | 2/2006 | Buehlmann et al. |
| 2006/0036234 A1 | 2/2006 | Durgin et al. |
| 2006/0052774 A1 | 3/2006 | Garrison et al. |
| 2006/0178670 A1 | 8/2006 | Woloszko et al. |
| 2007/0093812 A1 | 4/2007 | Hayashida et al. |
| 2007/0198011 A1 | 8/2007 | Sugita |
| 2007/0208339 A1* | 9/2007 | Arts ............... A61B 17/32056 606/47 |
| 2007/0270796 A2 | 11/2007 | Girard et al. |
| 2008/0009747 A1* | 1/2008 | Saadat ............... A61B 1/0008 600/471 |
| 2008/0077129 A1 | 3/2008 | Van Wyk et al. |
| 2008/0221587 A1 | 9/2008 | Schwartz |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0063500 A1 | 3/2010 | Muszala |
| 2010/0069903 A1 | 3/2010 | Allen, IV et al. |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0249769 A1 | 9/2010 | Nau, Jr. et al. |
| 2010/0280511 A1 | 11/2010 | Rachlin et al. |
| 2011/0034918 A1 | 2/2011 | Reschke |
| 2011/0054468 A1 | 3/2011 | Dycus |
| 2011/0054471 A1 | 3/2011 | Gerhardt et al. |
| 2011/0060333 A1* | 3/2011 | Mueller ............... A61B 17/295 606/46 |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0178515 A1 | 7/2011 | Bloom et al. |
| 2011/0319880 A1 | 12/2011 | Prakash et al. |
| 2013/0103041 A1 | 4/2013 | Regadas |
| 2014/0236142 A1 | 8/2014 | Ward et al. |

FOREIGN PATENT DOCUMENTS

| | | |
|---|---|---|
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10028850 C1 | 10/2001 |
| DE | 10045375 C2 | 10/2002 |
| DE | 19738457 B4 | 1/2009 |
| EP | 0467501 A1 | 1/1992 |
| EP | 1159926 A3 | 3/2003 |
| EP | 1645240 A2 | 4/2006 |
| EP | 1829494 A1 | 9/2007 |
| GB | 1490585 | 11/1977 |
| JP | 61-501068 | 9/1984 |
| JP | 65502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09010223 A | 1/1997 |
| JP | 10-014922 | 1/1998 |
| JP | 11-070124 A | 3/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 93/21845 | 11/1993 |
| WO | 0036986 A1 | 6/2000 |
| WO | 0154604 A1 | 8/2001 |
| WO | 02/007627 A1 | 1/2002 |
| WO | 2004/073753 A2 | 9/2004 |
| WO | 2004/103156 A2 | 12/2004 |
| WO | 2005/110264 A2 | 11/2005 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Reich, O., et al., "Ex-vivo comparison of the haemostatic properties of standard transurethral resection and transurethral vaporization resection of the prostate", BJU International, vol. 92, pp. 319-322 (2003).
Wendt-Nordahl, Gunnar et al., "The Vista System: A New Bipolar Resection Device for Endourological Procedures: Comparison with Conventional Resectoscope", European Urology, vol. 46, pp. 586-590 (2004).
Extended European Search Report from Application No. 14154456.9 dated Jun. 11, 2014.
Examination Report issued in corresponding application No. 14 154 456.9 dated Aug. 11, 2015.

* cited by examiner

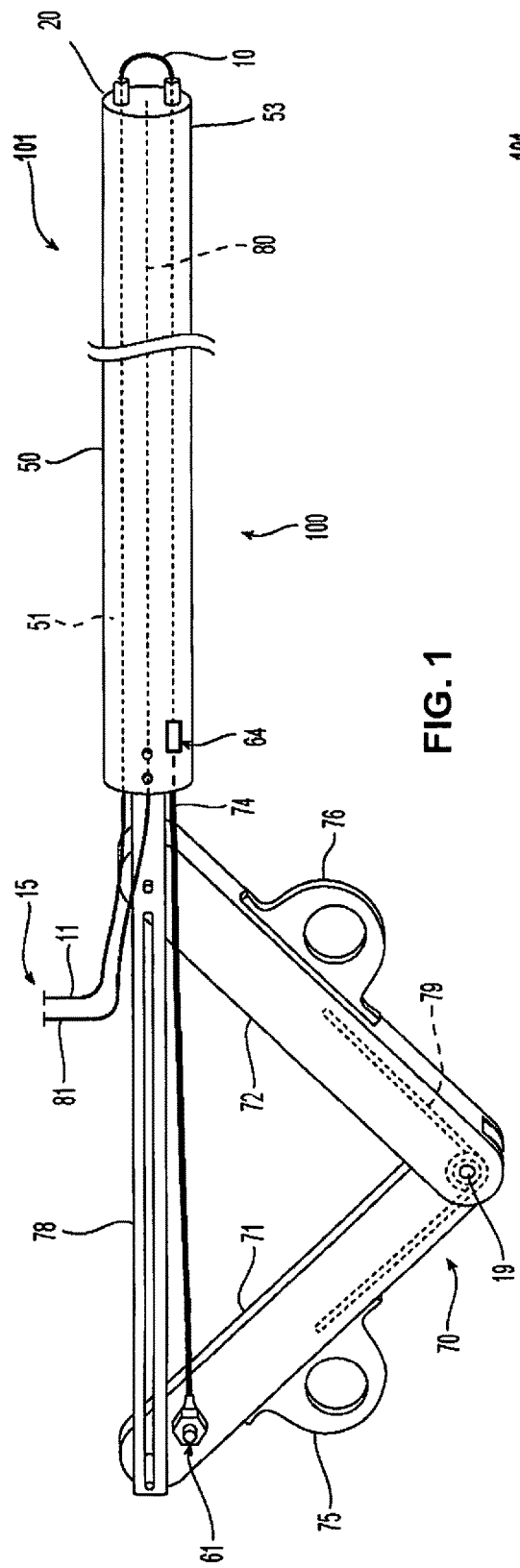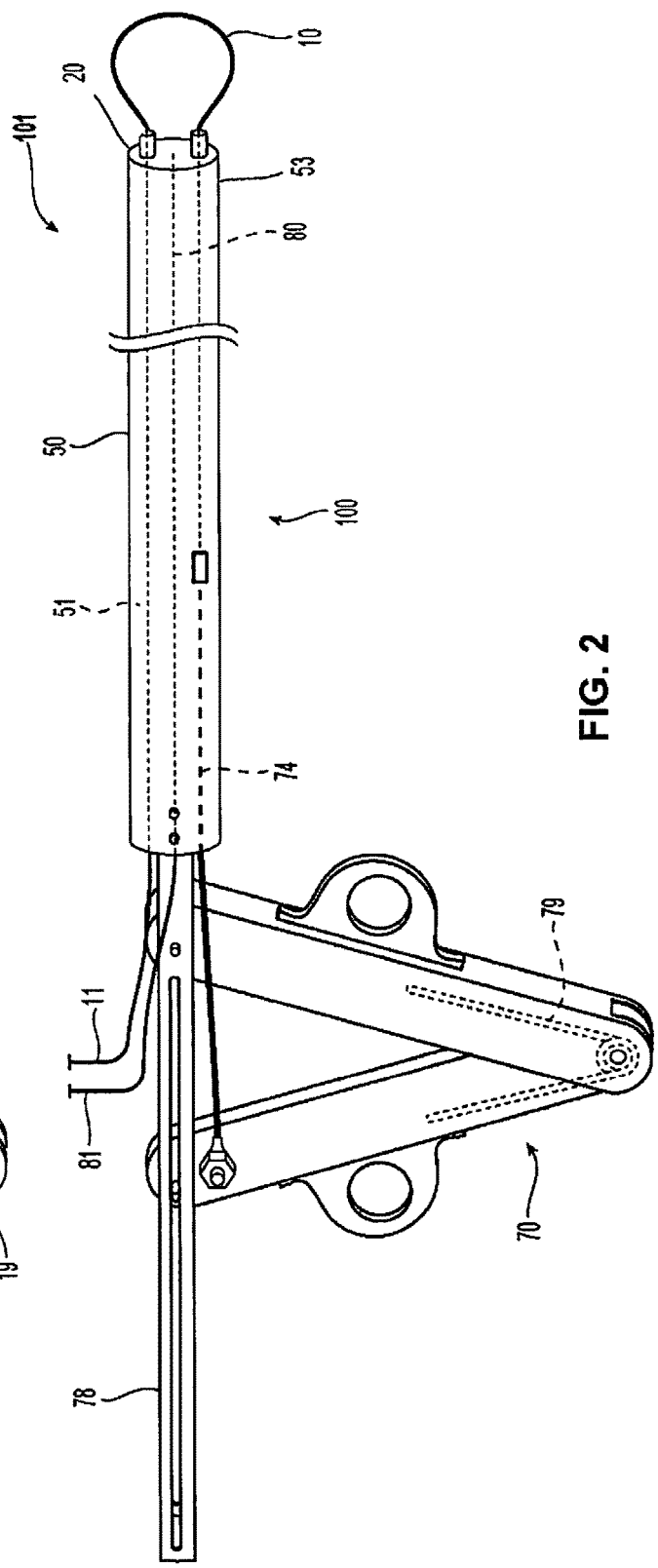

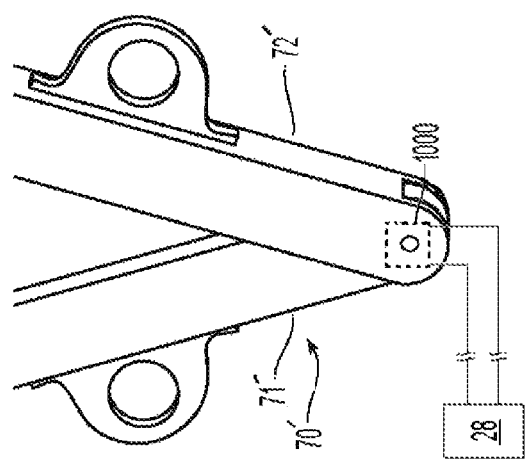

SINGLE-HANDED OPERABLE SURGICAL INSTRUMENT INCLUDING LOOP ELECTRODE WITH INTEGRATED PAD ELECTRODE

CROSS REFERENCE TO RELATED APPLICATION

The present application claims the benefit of and priority to U.S. Provisional Application Ser. No. 62/055,328, filed on Sep. 25, 2014, the entire contents of which are incorporated herein by reference.

BACKGROUND

1. Technical Field

The present disclosure relates to electrosurgical devices, such as soft tissue radio-frequency (RF) transection and resection devices. More particularly, the present disclosure relates to single-handed operable electrosurgical instruments including a loop electrode with an integrated pad electrode.

2. Discussion of Related Art

Electrosurgical methods are widely used in the operative field since electrosurgery generally reduces patient bleeding associated with tissue cutting, transecting and/or resecting procedures. Two widely accepted methods of electrosurgery are performed, namely, monopolar electrosurgery and bipolar electrosurgery.

In monopolar electrosurgery, devices use an instrument with a single, active electrode to deliver energy from an electrosurgical generator to tissue, and a patient return electrode or pad that is attached externally to the patient as the means to complete the electrical circuit between the electrosurgical generator and the patient. When the electrosurgical energy is applied, the energy travels from the active electrode, to the surgical site, through the patient and to the return electrode.

Alternatively, in bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit.

Monopolar tissue cutting devices such as snares are known which employ RF energy, applied between the snare loop and a grounding pad, to provide a cutting arc. The cutting arc passes through the tissue as the snare loop is tightened around the polyp cauterizing the lesion and assisting the snare in excising the polyp.

Bipolar snares have also been developed which are formed by two electrode wires electrically insulated from each other. Alternatively, a snare loop may be formed from a first electrode wire while a second electrode wire is exposed at an end of the lumen. As the bipolar snare is tightened around the polyp and RF energy is applied across the two electrodes, the polyp is severed from the surrounding tissue.

Various configurations of snares have been developed to position and tighten fine-gauge, flexible, adjustable wire loops around a region of tissue (e.g., polyps) through an endoscope for mechanical or electrosurgical resection and hemostasis. Gastrointestinal snares, for example, typically consist of a hollow tubular structure, e.g., a cannula, with one or more adjustable wire loops that protrude at the working end. The snare loops may be made of monofilament or braided wires that are attached at the proximal end to an electrosurgical (usually monopolar) unit that provides RF energy between the isolated metal loop, which functions as an active electrode, and an external neutral electrode to heat the tissue and facilitate resection and cauterization. During a supracervical hysterectomy, cervical transections can be one of the more difficult steps to the procedure. In order to save time and provide a smooth, uncharred cervical face, electrosurgical snares are often used. These are typically monopolar snares, which are operated two-handedly.

Transection and/or resection of soft tissues may pose particular difficulties during electrosurgical operations and may require unique electrosurgical instruments, systems, techniques and the like for operating thereon.

SUMMARY

The present disclosure is directed to single-handedly operable electrosurgical instruments including a loop electrode with an integrated pad electrode.

According to an aspect of the present disclosure, a bipolar electrosurgical instrument is provided and includes a handle portion, a shaft extending from the handle portion, a pad electrode coupled to the distal end of the shaft, and a loop electrode configured to be selectively transitioned from a deployed configuration, wherein the loop electrode extends outwardly from a distal end of the shaft in a manner capable of receiving tissue, to a non-deployed configuration, wherein the loop electrode is disposed proximate to the distal end of the shaft, to treat tissue.

According to an aspect of the present disclosure, a bipolar electrosurgical instrument is provided and includes a shaft, a pad electrode assembly coupled to the shaft, and a loop electrode configured to be selectively transitioned from a deployed configuration wherein the loop electrode extends outwardly from a distal end of the shaft in a manner capable of receiving tissue, to a non-deployed configuration, wherein the loop electrode is disposed proximate to the distal end of the shaft, to treat tissue. The pad electrode assembly includes an actuator member and one or more arm members. Each of the one or more arm members includes an end portion formed of an electrically-conductive material.

BRIEF DESCRIPTION OF THE DRAWINGS

Objects and features of the presently-disclosed single-handedly operable electrosurgical instrument including a loop electrode with an integrated pad electrode will become apparent to those of ordinary skill in the art when descriptions of various embodiments thereof are read with reference to the accompanying drawings, of which:

FIG. 1 is a perspective view of an electrosurgical instrument including a loop electrode with an integrated pad electrode in accordance with an embodiment of the present disclosure;

FIG. 2 is a perspective view of the electrosurgical instrument of FIG. 1 showing the loop electrode in a deployed configuration in accordance with an embodiment of the present disclosure;

FIG. 11 is a perspective view of another embodiment of a handle portion of the electrosurgical in instrument in accordance with the present disclosure.

DETAILED DESCRIPTION

Figure 3:
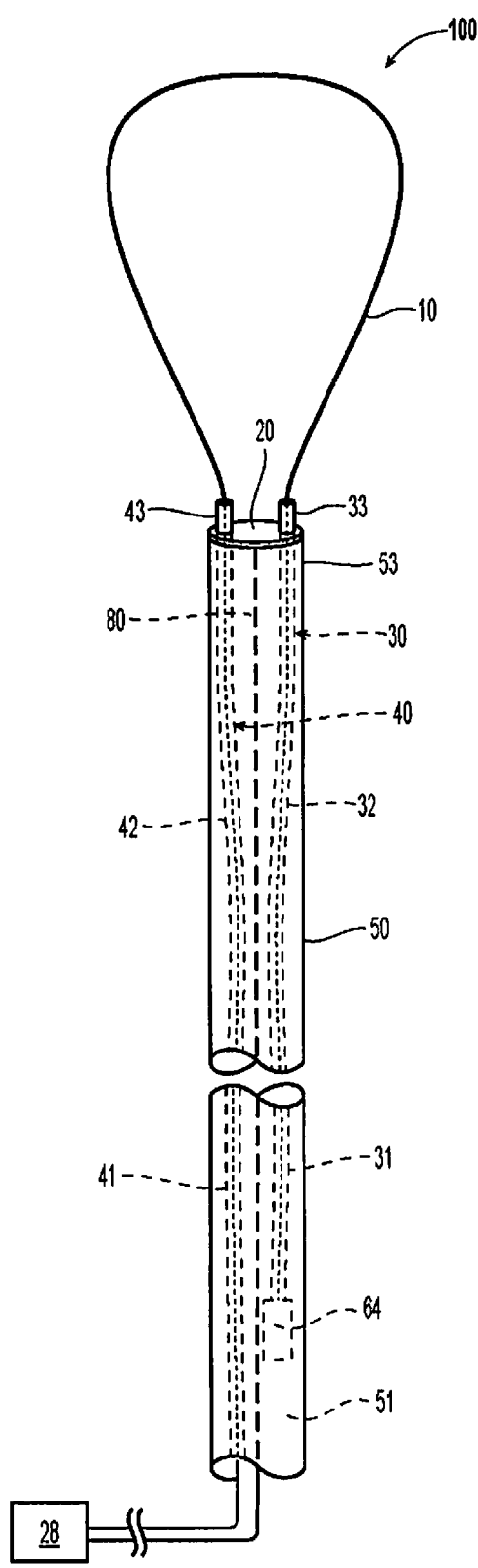
FIG. 3 is a perspective view of a portion of the electrosurgical instrument of FIG. 1 in accordance with an embodiment of the present disclosure.

Hereinafter, embodiments of the presently-disclosed single-handedly operable electrosurgical instrument including a loop electrode with an integrated pad electrode are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "electrically conductive," or simply "conductive," generally refers to materials that are capable of electrical conductivity, including, without limitation, materials that are highly conductive, e.g., metals and alloys, or materials that are semi-conductive, e.g., semi-conducting materials and composites.

Various embodiments of the present disclosure provide electrosurgical instruments configured to provide bipolar electrosurgical energy, which may be suitable for sealing, cauterizing, coagulating, desiccating, and/or cutting tissue. Embodiments of the presently-disclosed electrosurgical instruments may be suitable for utilization in endoscopic surgical procedures and/or suitable for utilization in open surgical applications. Embodiments of the presently-disclosed electrosurgical instruments include a loop electrode adapted to be selectively transitioned from a deployed configuration to a non-deployed configuration to treat tissue. Embodiments of the presently-disclosed electrosurgical instruments include a handle portion adapted to exert a biasing force on the loop electrode.

In FIGS. 1 and 2, an embodiment of an electrosurgical instrument 101 is shown for use with various surgical procedures and generally includes an energy-delivery portion 100 and a handle portion 70. Energy-delivery portion 100 includes an elongated shaft 50 defining a central lumen 51 therethrough, a pad electrode 20 disposed at the distal end 53 of the shaft 50, and a loop electrode 10. Loop electrode 10 is adapted to be selectively transitioned from a deployed configuration, as shown for example in FIG. 7A, to a non-deployed configuration, as shown for example in FIG. 7B, to treat tissue "T." An embodiment of the energy-delivery portion 100 of FIGS. 1 and 2 is shown in more detail in FIGS. 3 and 5. It is to be understood, however, that other energy-delivery portion embodiments (e.g., the energy-delivery portion 400 shown in FIG. 4, the energy-delivery portion 600 shown in FIG. 6, the energy-delivery portion 800 shown in FIGS. 8A-8C, and the energy-delivery portion 900 shown in FIG. 9) may also be used. One or more components of the electrosurgical instrument 101, e.g., the handle portion 70, the pad electrode 20, and the loop electrode 10, may be adapted to mutually cooperate to seal and/or divide tissue. Electrosurgical instrument 101 may include additional, fewer, or different components than shown in FIGS. 1 and 2, depending upon a particular purpose or to achieve a desired result.

Handle portion 70 generally includes a first arm member 71, a second arm member 72, and a guide member 78. The first and second arm members 71 and 72, respectively, are movably mounted about a pivot 19 that allows the first and second arm members 71 and 72 to pivot relative to one another. In some embodiments, as shown for example in FIGS. 1 and 2, the first arm member 71 is slideably coupled to the guide member 78. In addition, or alternatively, the second arm member 72 may be pivotally mounted to the guide member 78 in fixed relation to the proximal end of the energy-delivery portion 100. The shape and size of the first arm member 71 and the second arm member 72 may be varied from the configuration depicted in FIGS. 1 and 2.

In some embodiments, loop members 75 and 76 may be coupled to, or otherwise operably associated with, the first and second arm members 71 and 72, respectively. Each loop member 75 and 76 defines a finger and/or thumb hole therethrough for receiving the user's finger or thumb. Finger and/or thumb holes facilitate movement of first and second arm members 71 and 72 relative to one another to translate the loop electrode 10 from a non-deployed configuration, as shown for example in FIG. 1, to a deployed configuration, as shown for example in FIG. 2, and/or to translate the loop electrode 10 from a deployed configuration, as shown for example in FIG. 7A, to a non-deployed configuration, as shown for example in FIG. 7B, to treat tissue "T."

Electrosurgical instrument 101 includes a linkage 74, e.g., an elongated, rod-like or wire-like member, coupled to the first arm member 71 and extending distally therefrom. In some embodiments, as shown for example in FIGS. 1 and 2, the distal end of the linkage 74 is disposed within the central lumen 51 of the shaft 50. As can be appreciated, applying force to move the first arm member 71 toward the second arm member 72 pushes the linkage member 74 distally, which, in turn, translates the loop electrode 10 to a deployed configuration wherein the loop electrode 10 extends outwardly from a distal end 53 of the shaft 50, e.g., in a manner capable of receiving tissue. Linkage 74 may be operatively connected to one end of electrode 10 as shown or a second linkage may be connected to the other end of electrode 10.

In some embodiments, as shown for example in FIGS. 1 and 2, a biasing member 79 is provided (e.g., disposed within the handle portion 70) and configured to bias the loop electrode 10. In some embodiments, the biasing member 79 may be different types of springs, e.g., a torsion spring, or other structures that provide biasing characteristics. In some embodiments, the biasing member 79 is configured to exert a constant force or a near-constant force on the loop electrode 10. In other embodiments, the biasing member 79 may be an electric motor, in which case, a switch (not shown) may be provided, e.g., operably associated with the handle portion 70, to enable the user to selectively activate the biasing member 79. As can be appreciated, allowing the first arm member 71 to move away from the second arm member 72, under the force exerted by the biasing member 79, pulls the linkage member 74 proximally, which, in turn, translates the loop electrode 10 to a non-deployed configuration, wherein the loop electrode 10 is disposed proximate to the distal end 53 of the shaft 50.

Electrosurgical instrument 101 includes a transmission line, which may connect directly to an electrosurgical energy source 28. The transmission line may be formed from a suitable flexible, semi-rigid, or rigid cable, and may be internally divided into one or more cable leads, e.g., leads each of which transmits bipolar energy through their respective feed paths to the loop electrode 10 and the pad electrode 20 as associated with energy source 28. In some embodiments, the loop electrode 10 and the pad electrode 20 are electrically coupled to opposite terminals, e.g., positive or active (+) and negative or return (−) terminals associated with the electrosurgical energy source 28. In this manner, bipolar energy may be provided through the loop electrode 10 and the pad electrode 20 to tissue. Electrosurgical energy source 28 may be any generator suitable for use with electrosurgical devices. Examples of generators that may be suitable for use as a source of RF energy are commercially available under the trademark FORCE TRIAD™ offered by Covidien Surgical Solutions of Boulder, Colo. Electrosurgical instrument 101 may alternatively be configured as a wireless device or battery-powered.

Figure 4:
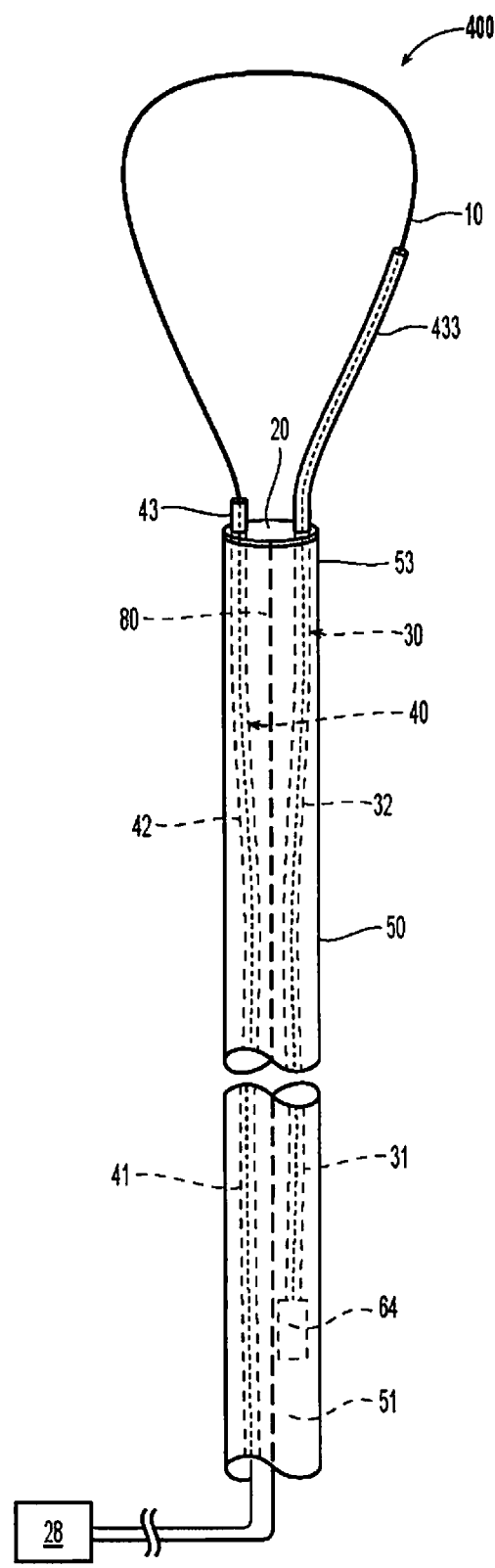
FIG. 4 is a perspective view of another embodiment of a portion of an electrosurgical instrument in accordance with the present disclosure.

As shown in FIG. 3, energy-delivery portion 100 generally includes a first tubular member 30 and a second tubular member 40. First and second tubular members 30 and 40 are configured to moveably receive the loop electrode 10 therein. First tubular member 30 includes an end portion 33 that extends from the distal end 53 of the shaft 50 and includes an elongated portion 32 (shown in phantom lines in FIG. 3) disposed within the central lumen 51 of the shaft 50. Second tubular member 40 includes an end portion 43 that extends from the distal end 53 of the shaft 50 and includes an elongated portion 42 (shown in phantom lines in FIG. 3) disposed within the central lumen 51 of the shaft 50. In some embodiments, the first tubular member 30 may include a portion 31 disposed within the handle portion 70, and/or the second tubular member 40 may include a portion 41 disposed within the handle portion 70. First and second tubular members 30 and 40 may be formed of any suitable electrically non-conductive material. In some embodiments, the first and second tubular members 30 and 40 may be formed of polytetrafluoroethylene (PTFE) (e.g., Teflon®, manufactured by E. I. du Pont de Nemours and Company of Wilmington, Del., United States).

Loop electrode 10 and the pad electrode 20 may be formed of any suitable electrically-conductive material. In some embodiments, the pad electrode 20 may be made of a metal or alloy, e.g., phosphor bronze, and may have a thickness of about 10 millimeters. In some embodiments, the loop electrode 10 is made from tungsten or stainless steel, and may have an outer diameter that ranges from about 0.009 inches to about 0.014 inches.

Pad electrode 20 may be coupled to the shaft 50 in any suitable manner, e.g., adhesively bonded and/or welded. Electrosurgical instrument 101 generally includes an electrical lead 80, e.g., a wire, electrically-coupled to the pad electrode 20. Electrical lead 80 may be electrically-coupled to the pad electrode 20 by any suitable manner of electrical connection, e.g., soldering, welding, or laser welding. It is to be understood that the dashed lines indicative of electrical connections (e.g., electrical conductors) between various components of the energy-delivery portion 100 are merely illustrative and non-limiting examples of electrical connections, and that energy-delivery portion embodiments of the present disclosure may utilize many different configurations of electrical connections, some with fewer, or additional, electrical connections than depicted in FIGS. 1 through 3.

Figure 5:
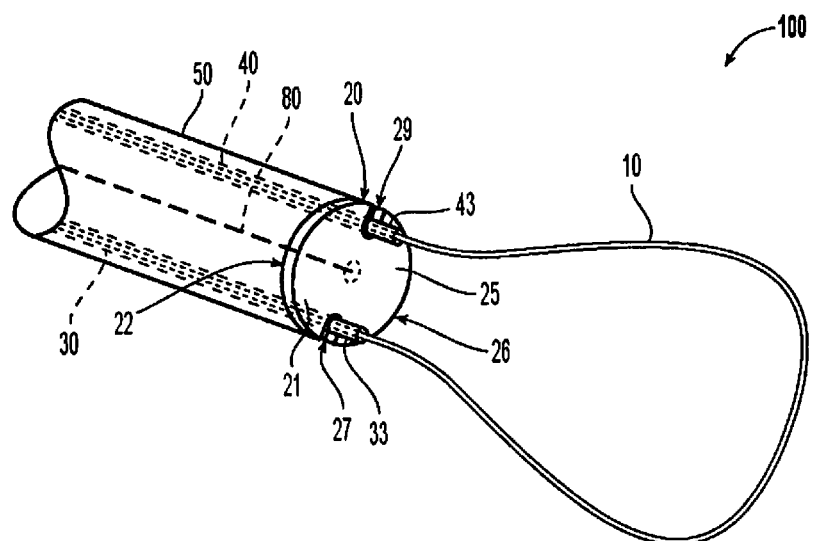
FIG. 5 is a perspective view of a portion of the electrosurgical instrument of FIG. 1 showing the loop electrode and the pad electrode in accordance with an embodiment of the present disclosure.

As shown in FIG. 5, the pad electrode 20 includes a first portion 21 having a first convex edge 22 and a second portion 25 having a second convex edge 26. First and second convex edges 22 and 26 are spaced apart from one another by first and second openings 27 and 29, respectively, defined therebetween. In some embodiments, the first and second openings 27 and 29 are configured to allow portions (e.g., end portions 33 and 43) of the first and second tubular members 30 and 40, respectively, to pass therethrough. End portions 33 and 43 of the first and second tubular members 30 and 40, respectively, may be configured to electrically-isolate the loop electrode 10 from the pad electrode 20. In some embodiments, the end portions 33 and 43 of the first and second tubular members 30 and 40, respectively, may be configured to extend about 0.06 inches distally from the pad electrode 20. End portions 33 and 43 may additionally, or alternatively, be configured to protrude at an angle slightly outward from the surface normal of the pad electrode 20.

In some embodiments, the outer diameter of the pad electrode 20 may be substantially the same as the outer diameter of the shaft 50. In some embodiments, the first and second openings 27 and 29 are generally slot-shaped with a width of about 0.05 inches and a length of about 0.06 inches. The shape and size of the first opening 27 and the second opening 29 may be varied from the configuration depicted in FIG. 5.

Figure 7A:
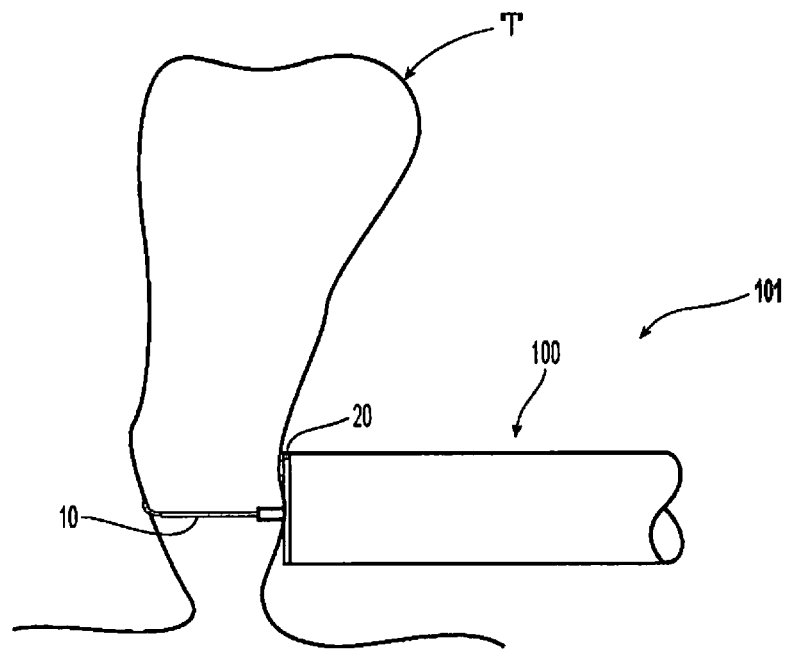
FIG. 7A is a schematic view of a portion of the electrosurgical instrument of FIG. 1 with the loop electrode in a deployed configuration and the pad electrode disposed proximate to tissue to be cut in accordance with an embodiment of the present disclosure.

Once tissue "T" is properly positioned within the loop electrode 10 and the pad electrode 20 is positioned adjacent to tissue "T" to be cut, as illustratively depicted in FIG. 7A, the loop electrode 10 functions as an active electrode and the pad electrode 20 functions as a return electrode during activation such that energy flows from the active electrode through tissue "T" positioned within the loop electrode 10 to the return electrode. During operation of the electrosurgical instrument 101, the loop electrode 10 is selectively transitioned from a deployed configuration (FIG. 7A) to a non-deployed configuration (FIG. 7B), e.g., to sever tissue "T."

Figure 6:
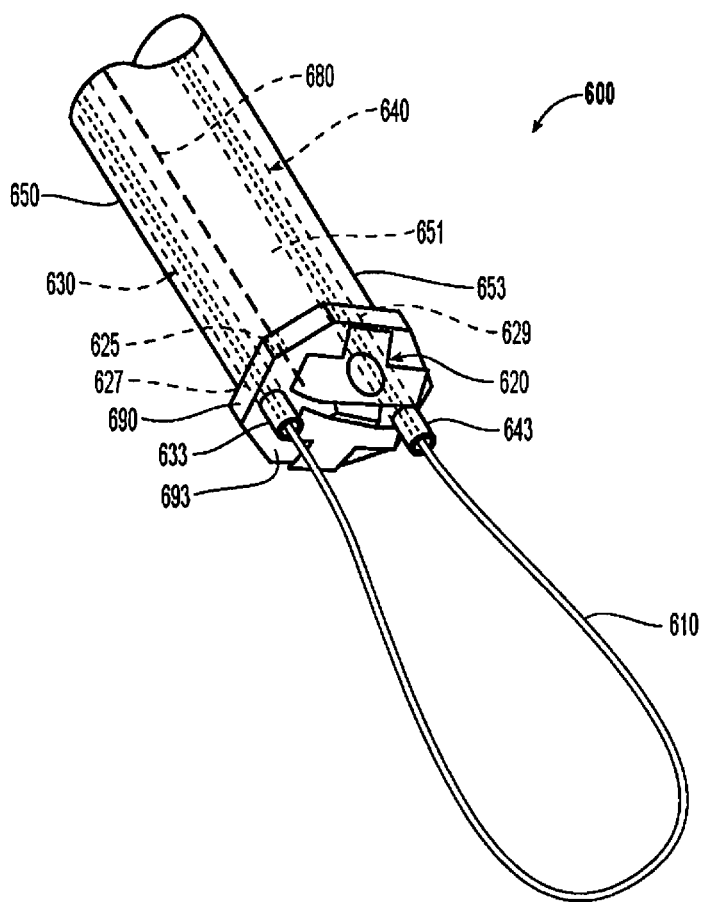
FIG. 6 is a perspective view of a portion of an electrosurgical device in accordance with another embodiment of the present disclosure.
Figure 7B:
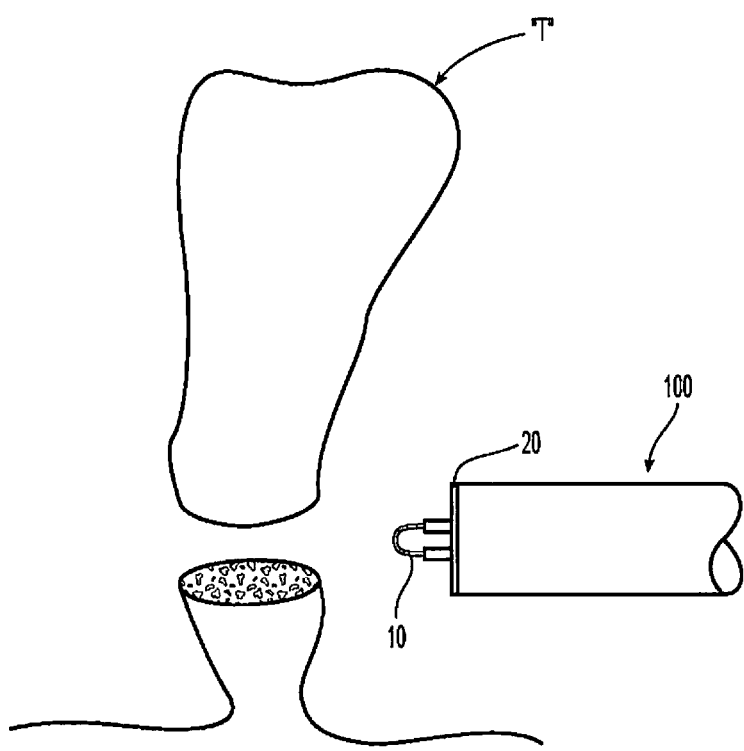
FIG. 7B is a schematic view of a portion of the electrosurgical instrument of FIG. 1 after transaction of tissue with the loop electrode in a non-deployed configuration in accordance with an embodiment of the present disclosure.

In FIG. 6, an energy-delivery portion 600 of an electrosurgical instrument is shown for use with various surgical procedures and generally includes an elongated shaft 650, a support structure 690 disposed at the distal end 653 of the shaft 650, a pad electrode 620 coupled to the support structure 690, and a loop electrode 610. As shown in FIG. 6, energy-delivery portion 600 includes a first tubular member 630 and a second tubular member 640. First and second tubular members 630 and 640 are configured to moveably receive the loop electrode 610 therein, and may be formed of any suitable electrically non-conductive material. Energy-delivery portion 600 may include any feature or combination of features of the energy-delivery portion embodiments disclosed herein.

Support structure 690 may be formed of any suitable material or combination of materials, and may be formed by any suitable process, e.g., injection molding. In some embodiments, the support structure 690 is formed of an electrically non-conductive material such as polymeric materials, e.g., plastics, and/or other insulative materials. Support structure 690 includes first and second apertures 627 and 629 defined therethrough. In some embodiments, the first and second apertures 627 and 629 are configured to receive a portion of the first and second tubular members 630 and 640, respectively, therein. Support structure 690 may include a third aperture 625 configured to facilitate an electrical connection between the electrical lead 680 and the pad electrode 620. In some embodiments, the support structure 690 may be overmolded onto the distal end 653 of the shaft 650.

In some embodiments, the first and second tubular members 630 and 640 include an end portion 633 and 643, respectively, that extends from the distal side 693 of the support structure 690. End portions 633 and 643 of the first and second tubular members 630 and 640, respectively, may be configured to electrically-isolate the loop electrode 610 from the pad electrode 620. Support structure 690 may additionally, or alternatively, be configured to electrically-isolate the loop electrode 610 from the pad electrode 620.

Figure 8A:
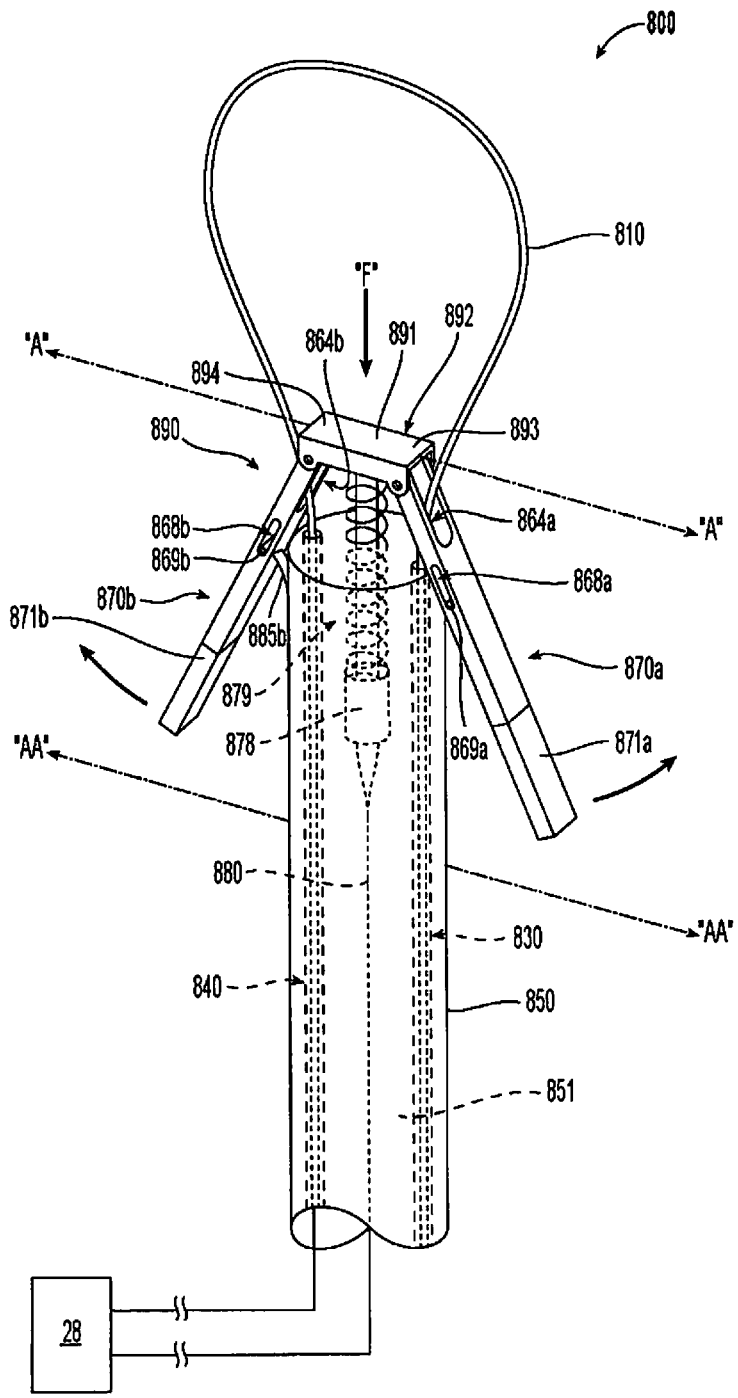
FIG. 8A is a perspective view of a portion of an electrosurgical instrument in a first configuration in accordance with another embodiment of the present disclosure.
Figure 8B:
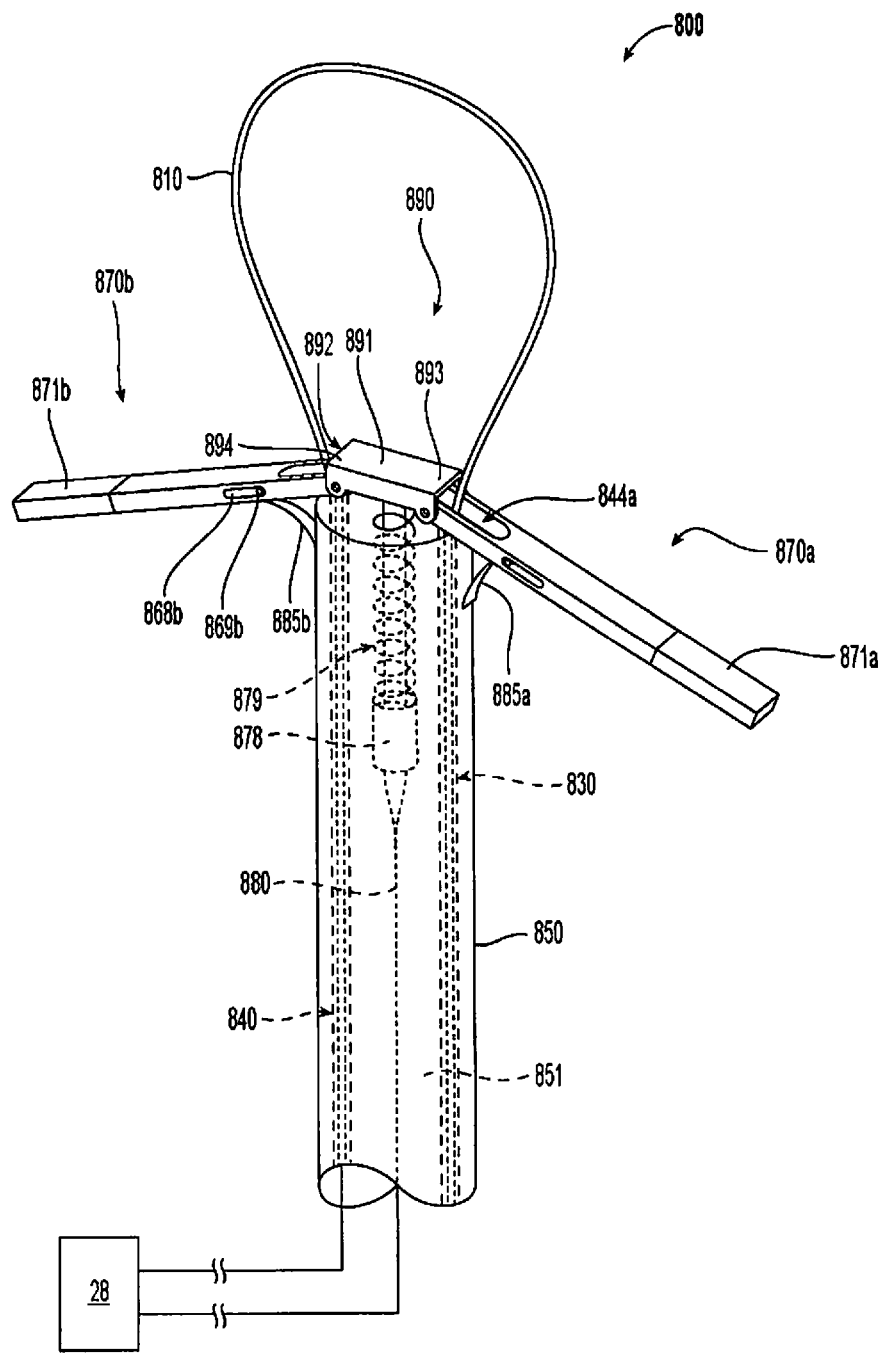
FIG. 8B is a perspective view of the electrosurgical instrument of FIG. 8A in a second configuration in accordance with the present disclosure.
Figure 8C:
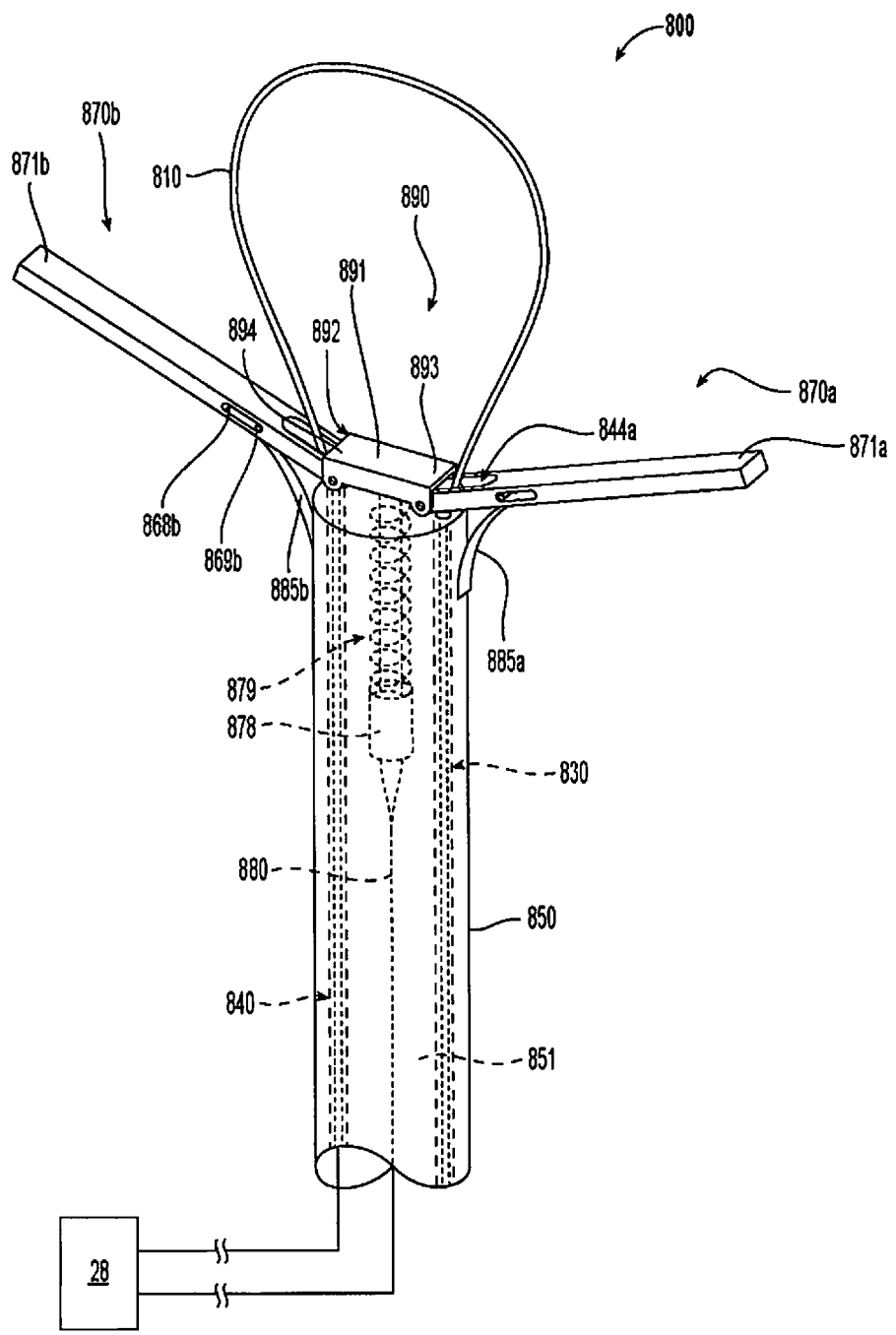
FIG. 8C is a perspective view of the electrosurgical instrument of FIG. 8A in a third configuration in accordance with the present disclosure.

In FIGS. 8A-8C, an energy-delivery portion 800 of an electrosurgical instrument is shown for use with various surgical procedures and generally includes a loop electrode 810, a pad electrode assembly 890, and an elongated shaft 850 defining a central lumen 851 therethrough. Energy-delivery portion 800 includes a first tubular member 830 and a second tubular member 840. First and second tubular members 830 and 840 are disposed within the lumen 851 of the shaft 850 and configured to moveably receive the loop electrode 810 therein, and may be formed of any suitable electrically non-conductive material. Loop electrode 810 and the first and second tubular members 830 and 840 are similar to the loop electrode 10 and the first and second tubular members 30 and 40, respectively, shown in FIG. 1. Further description of like elements is omitted in the interests of brevity. Energy-delivery portion 800 may include any feature or combination of features of the energy-delivery portion embodiments disclosed herein.

Pad electrode assembly 890 generally includes an actuator member 892 having a first end 893 and a second end 894 disposed opposite the first end 893. As shown in FIG. 8A, the actuator member 892 defines a longitudinal axis "A-A", wherein the longitudinal axis "A-A" is substantially parallel to or aligned with a traverse axis "AA-AA" defined by the first and second tubular members 830 and 840. The shape and size of the actuator member 892 may be varied from the configuration depicted in FIGS. 8A-8C.

In some embodiments, the pad electrode assembly 890 includes two arm members 870a and 870b (also referred to herein as "first and second arm members 870a and 870b") moveably coupled to the first and second ends 893 and 894, respectively, of the actuator member 892. First and second arm members 870a and 870b may be pivotably mounted with respect to the actuator member 892, e.g., mounted about pivot pins (not explicitly shown). First and second arm members 870a and 870b may additionally, or alternatively, be configured to be moveably coupled to the shaft 850.

First and second arm members 870a and 870b may be formed of any suitable material or combination of materials. In some embodiments, one or more portions of the first and second arm members 870a and 870b (e.g., end portions 871a and 871b, respectively) may be formed of an electrically-conductive material. The shape and size of the electrically-conductive portions of the first and second arm members 870a and 870b may be varied from the configuration depicted in FIGS. 8A-8C.

First and second arm members 870a and 870b define first and second apertures 864a and 864b, respectively, configured to allow the loop electrode 810 to pass therethrough. In some embodiments, as shown for example in FIGS. 8A-8C, the first and second apertures 864a and 864b are generally slot-shaped openings associated with portions of the first and second arm members 870a and 870b disposed proximate to the first and second ends 893 and 894, respectively, of the actuator member 892. The shape, size, and relative position (e.g., in relation to actuator member 892) of the first and second apertures 864a and 864b may be varied from the configuration depicted in FIGS. 8A-8C.

In some embodiments, as shown for example in FIGS. 8A-8C, the pad electrode assembly 890 includes elongated slots 868a and 868b defined in side portions of the first and second arm members 870a and 870b, respectively, and pins 869a and 869b operably engaged with the elongated slots 868a and 868b, respectively. As shown in FIG. 8A, the pins 869a and 869b are coupled to attachment members 885a and 885b, respectively, which, in turn, are coupled to the shaft 850. In some embodiments, the attachment members 885a and 885b may be formed of an elastomeric material. In other embodiments, portions of the attachment members 885a and 885b may be slideably receivable with the central lumen 851 of the shaft 850.

Pad electrode assembly 890 may include one or more arm members (e.g., two arm members 870a and 870b) of varied geometries, e.g., lengths and curvatures, or having additional, fewer, or different features than the first and second arm members 870a and 870b, such that variously-configured pad electrode assemblies may be fabricated and assembled, e.g., depending upon design of specialized electrosurgical instruments.

Actuator member 892 may be formed of any suitable material or combination of materials. For example, the actuator member 892 may include an electrically-conductive tissue-engaging surface 891 disposed between the first end 893 and the second end 894 thereof. One or more portions of the surfaces of the actuator member 892 may include an electrically non-conductive material, e.g., electrically-insulative coating. In some embodiments, the actuator member 892 may be formed entirely of an electrically non-conductive material.

In some embodiments, as shown for example in FIGS. 8A-8C, the energy-delivery portion 800 includes a biasing member 879 coupled to the actuator member 892. A centering bearing 878 may be coupled between the electrical lead 880 and the biasing member 879.

Pad electrode assembly 890 is adapted to be transitioned, upon the application of force "F" to the actuator member 892 (as indicated by the straight arrow in FIG. 8A), from a first configuration (FIG. 8A) wherein the first and second arm members 870a and 870b are positioned proximate to the shaft 850, to one or more different configurations (e.g., a second configuration shown in FIG. 8B and a third configuration shown in FIG. 8C) wherein the first and second arm members 870a and 870b are extended outwardly in relation to the shaft 850 (as indicated by the curved arrows in FIG. 8A). As shown in FIGS. 8A-8C, the first and second apertures 864a and 864b of the first and second arm members 870a and 870b are configured to allow the loop electrode 810 to pass therethrough when the pad electrode assembly 890 is disposed in the first configuration (FIG. 8A), the second configuration (FIG. 8B), or the third configuration (FIG. 8C).

In some embodiments, the loop electrode 810 and one or more portions of the pad electrode assembly 890 (e.g., end portions 871a and 871b of the first and second arm members 870a and 870b, respectively) are electrically coupled to opposite terminals, e.g., positive or active (+) and negative or return (−) terminals associated with an electrosurgical energy source (e.g., energy source 28 shown in FIG. 3). In some embodiments wherein the first and second arm members 870a and 870b include electrically-conductive end portions 871a and 871b, respectively, when the pad electrode assembly 890 is disposed in the second configuration, as shown in FIG. 7, the loop electrode 810 functions as an active electrode and the end portions 871a and 871b function as return electrodes during activation such that energy flows from the active electrode through tissue positioned within the loop electrode 810 to the return electrodes.

In some embodiments, the distal end of the shaft 850 may be covered by any suitable material. Electrosurgical instrument 800 may include additional, fewer, or different components than shown in FIGS. 8A-8C, depending upon a particular purpose or to achieve a desired result.

Figure 9:
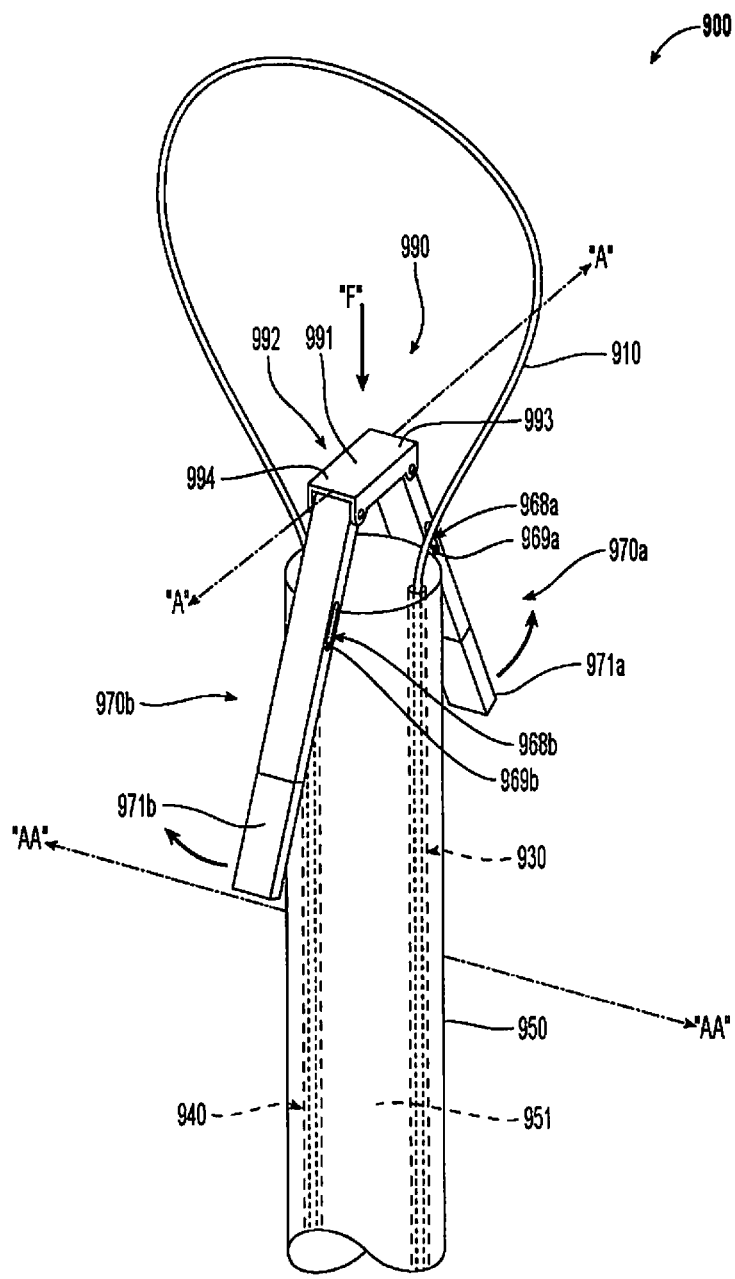
FIG. 9 is a perspective view of a portion of another embodiment of an electrosurgical instrument in accordance with the present disclosure.

In FIG. 9, an energy-delivery portion 900 of an electrosurgical instrument is shown for use with various surgical procedures and includes a pad electrode assembly 990. Energy-delivery portion 900 generally includes a loop electrode 910, an elongated shaft 950, and first and second tubular members 930 and 940. Loop electrode 910, the elongated shaft 950, and the first and second tubular members 930 and 940 are similar to the loop electrode 810, the elongated shaft 850, and the first and second tubular members 830 and 840, respectively, shown in FIGS. 8A-8C. Further description of like elements is omitted in the interests of brevity. Energy-delivery portion 900 may include any feature or combination of features of the energy-delivery portion embodiments disclosed herein.

Pad electrode assembly 990 generally includes an actuator member 992 having a first end 993 and a second end 994 disposed opposite the first end 993. As shown in FIG. 9, actuator member 992 defines a longitudinal axis "A-A", wherein the longitudinal axis "A-A" is substantially perpendicular to the traverse axis "AA-AA" defined by the first and second tubular members 630 and 640. The shape and size of the actuator member 992 may be varied from the configuration depicted in FIG. 9.

In comparison to the energy-delivery portion 800 shown in FIGS. 8A-8C, wherein the longitudinal axis "A-A" defined by the pad electrode assembly 890 is substantially parallel to the traverse axis "AA-AA" defined by the first and second tubular members 830 and 840, the pad electrode assembly 990 of FIG. 9 may include one or more arm members configured to position return electrodes along a direction orthogonal to the loop electrode 910 (i.e., as opposed to in alignment with the loop electrode 910).

In some embodiments, as shown for example in FIG. 9, the pad electrode assembly 990 includes two arm members 970a and 970b (also referred to herein as "first and second arm members 970a and 970b") moveably coupled to the first and second ends 993 and 994, respectively, of the actuator member 992. First and second arm members 970a and 970b may be pivotably mounted with respect to the actuator member 992, e.g., mounted about pivot pins (not explicitly shown).

First and second arm members 970a and 970b may be formed of any suitable material or combination of materials. In some embodiments, one or more portions of the first and second arm members 970a and 970b (e.g., end portions 971a and 971b, respectively) may be formed of an electrically-conductive material. The shape and size of the electrically-conductive portions the first and second arm members 970a and 970b may be varied from the configuration depicted in FIG. 9.

In some embodiments, as shown for example in FIG. 9, the pad electrode assembly 990 includes elongated slots 968a and 968b defined in side portions of the first and second arm members 970a and 970b, respectively, and pins 969a and 969b operably engaged with the elongated slots 968a and 968b, respectively. Pins 969a and 969b are coupled to attachment members (e.g., attachment members 885a and 885b, respectively, shown in FIG. 8A) which, in turn, are coupled to the shaft 950.

Pad electrode assembly 990 may include one or more arm members (e.g., two arm members 970a and 970b) of varied geometries, e.g., lengths and curvatures, or having additional, fewer, or different features than the first and second arm members 970a and 970b, such that variously-configured pad electrode assemblies may be fabricated and assembled, e.g., depending upon design of specialized electrosurgical instruments.

Actuator member 992 may be formed of any suitable material or combination of materials. For example, the actuator member 992 may include an electrically-conductive tissue-engaging surface 991 disposed between the first end 993 and the second end 994 thereof. One or more portions of the surfaces of the actuator member 992 may include an electrically non-conductive material, e.g., electrically-insulative coating. In some embodiments, the actuator member 992 may be formed entirely of an electrically non-conductive material.

Pad electrode assembly 990 is adapted to be transitioned, upon the application of force "F" to the actuator member 992 (as indicated by the straight arrow in FIG. 9), from a first configuration (FIG. 9) wherein the first and second arm members 970a and 970b are positioned proximate to the shaft 950, to at least a second configuration wherein the first and second arm members 970a and 970b are extended outwardly in relation to the shaft 950 (as indicated by the curved arrows in FIG. 9).

Figure 10:
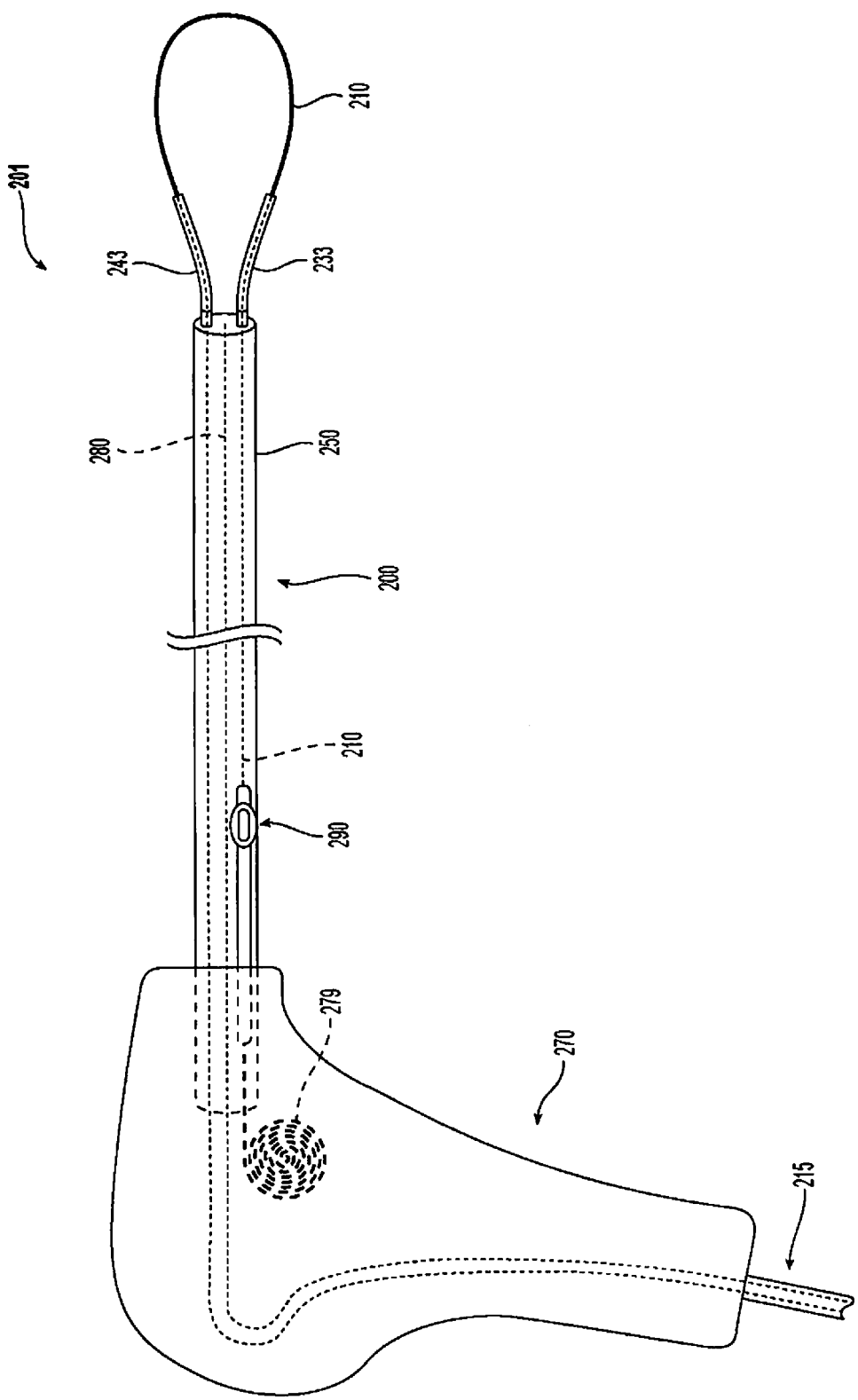
FIG. 10 is a perspective view of another embodiment of an electrosurgical instrument including a loop electrode with an integrated pad electrode in accordance with the present disclosure.

In FIG. 10, an embodiment of an electrosurgical instrument 201 is shown for use with various surgical procedures and generally includes an energy-delivery portion 200 including an elongated shaft 250, a pad electrode 220 disposed at the distal end of the shaft 250, tubular portions 233 and 243 extending distally from the shaft, and a loop electrode 210. Loop electrode 210 is adapted to be selectively transitioned from a deployed configuration to a non-deployed configuration to treat tissue (e.g., tissue "T" shown in FIGS. 7A and 7B). Loop electrode 210, the pad electrode 220, the tubular portions 233 and 243, and the shaft 250 are similar to the loop electrode 10, the pad electrode 20, the tubular portions 33 and 43, and the shaft 50, respectively, shown in FIGS. 1 and 2. Further description of like elements is omitted in the interests of brevity. Energy-delivery portion 200 may include any feature or combination of features of the energy-delivery portion embodiments disclosed herein.

Electrosurgical instrument 201 generally includes a handle portion 270 configured to support the shaft 250. The shape and size of the handle portion 270 may be varied from the configuration depicted in FIG. 10. Electrosurgical instrument 201 includes a transmission line 215, which may connect directly to an energy source (e.g., electrosurgical energy source 28 shown in FIG. 3). The transmission line may be formed from a suitable flexible, semi-rigid, or rigid cable, and may be internally divided into one or more cable leads (e.g., leads each of which transmits energy through their respective feed paths to the loop electrode 210 and the pad electrode 220.

Electrosurgical instrument 201 includes a slide member 290 slidably coupled to the shaft 250. Slide member 290 is coupled at its distal end to the loop electrode 210. In some embodiments, as shown for example in FIG. 10, a biasing member 279 is provided (e.g., disposed within the handle portion 270) and configured to bias the slide member 290 and/or the loop electrode 210. In some embodiments, the biasing member 279 may be different types of springs, e.g., a torsion spring, or other structures that provide biasing characteristics. In some embodiments, the biasing member 279 is configured to exert a constant force or a near-constant force on the slide member 290 and/or the loop electrode 210. As can be appreciated, allowing the slide member 290 to move proximally under the force exerted by the biasing member 279 translates the loop electrode 210 to a non-deployed configuration.

In FIG. 11, an embodiment of a handle member 70' including a first arm member 71' and a second arm member 72' is shown. Handle member 70' includes a sensor 1000 electrically coupled to generator 28. Sensor 1000 may be a potentiometer or switch that outputs a signal indicative of the position of the first arm member 71' relative to the second arm member 72'. The position of the first arm member 71' relative to the second arm member 72' is indicative of a position of the loop electrode 10. Based on the signal outputted to generator 28, generator 28 may alter the bipolar energy output and terminate the bipolar energy output once the tissue "T" is thoroughly cut through.

The above-described single-handed operable electrosurgical instruments are configured to provide bipolar electrosurgical energy and include a shaft and a loop electrode with an integrated pad electrode. The above-described loop electrode is configured to be selectively transitioned from a deployed configuration, wherein the loop electrode extends outwardly from a distal end of the shaft in a manner capable of receiving tissue, to a non-deployed configuration, wherein the loop electrode is disposed proximate to the distal end of the shaft.

The above-described electrosurgical instruments configured to provide bipolar electrosurgical energy may be suitable for utilization in endoscopic surgical procedures and/or suitable for utilization in open surgical applications.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely-steerable systems, automatically flexible surgical systems, remotely-flexible surgical systems, remotely-articulating surgical systems, wireless surgical systems, modular or selectively configurable remotely-operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although embodiments have been described in detail with reference to the accompanying drawings for the purpose of illustration and description, it is to be understood that the disclosed processes and apparatus are not to be construed as limited thereby. It will be apparent to those of ordinary skill in the art that various modifications to the foregoing embodiments may be made without departing from the scope of the disclosure.

What is claimed is:

1. A bipolar electrosurgical instrument, comprising:
   a handle portion;
   a shaft extending from the handle portion, the shaft including a distal end and defining a longitudinal axis;
   a pad electrode coupled to the distal end of the shaft and extending in a plane transverse to the shaft such that the longitudinal axis of the shaft extends through the pad electrode, the pad electrode defining a first opening and a second opening therethrough; and
   a loop electrode configured to be selectively transitioned between a deployed configuration and a non-deployed configuration to treat tissue, wherein in the deployed configuration, the loop electrode extends outwardly from a distal end of the shaft in a manner capable of receiving tissue, and in the non-deployed configuration, the loop electrode is disposed proximate to the distal end of the shaft, the loop electrode having a first end and a second end, the first end extending through the first opening of the pad electrode, the second end extending through the second opening of the pad electrode; and a torsion spring disposed in the handle portion, the torsion spring configured to exert a force on the loop electrode.

2. The bipolar electrosurgical instrument of claim 1, further comprising:

a first tubular member, the first tubular member at least partially disposed within a lumen defined by the shaft; and a second tubular member, the second tubular member at least partially disposed within the lumen defined by the shaft, wherein the first and second tubular members are configured to receive the loop electrode therein.

3. The bipolar electrosurgical instrument of claim 2, wherein the first tubular member and the second tubular member are moveable within the shaft.

4. The bipolar electrosurgical instrument of claim 2, wherein the first tubular member includes an end portion that extends from the distal end of the shaft.

5. The bipolar electrosurgical instrument of claim 4, wherein the second tubular member includes an end portion that extends from the distal end of the shaft.

6. The bipolar electrosurgical instrument of claim 5, wherein the end portions of the first and second tubular members are configured to electrically-isolate the loop electrode from the pad electrode.

7. The bipolar surgical instrument of claim 1, wherein the handle member includes a sensor configured to indicate a position of the loop electrode.

\* \* \* \* \*